(12) United States Patent
Satake et al.

(10) Patent No.: US 6,649,767 B2
(45) Date of Patent: Nov. 18, 2003

(54) PROCESS FOR PREPARING 1,4-DIHYDROPYRIDINE COMPOUNDS

(75) Inventors: Kunio Satake, Handa (JP); Noriaki Murase, Anjo (JP)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/224,928

(22) Filed: Aug. 20, 2002

(65) Prior Publication Data

US 2003/0078430 A1 Apr. 24, 2003

Related U.S. Application Data

(63) Continuation of application No. 09/716,158, filed on Nov. 17, 2000, now abandoned.
(60) Provisional application No. 60/170,217, filed on Dec. 10, 1999.

(51) Int. Cl.[7] .............................................. C07D 213/02
(52) U.S. Cl. ...................... 546/249; 546/286; 546/287; 546/318; 546/321
(58) Field of Search ............................... 546/249, 286, 546/287, 318, 321

(56) References Cited

FOREIGN PATENT DOCUMENTS

WO   WO 96/25689 A1 *   5/1999   ......... C07D/211/90

* cited by examiner

Primary Examiner—Zinna Northington Davis
(74) Attorney, Agent, or Firm—Scully, Scott, Murphy & Presser

(57) ABSTRACT

A process for preparing a 1,4-dihydropyridine compound comprising contacting an enamine compound

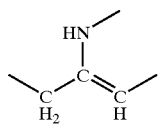

and a compound having a structure of

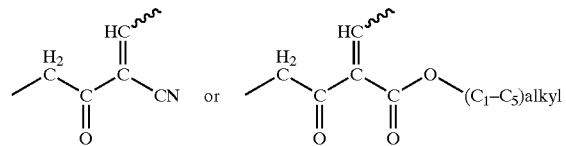

in the presence of a base; and treating the reaction mixture thus obtained in the presence of an acid or a combination of acids under mild reaction conditions. A resulting 1,4-dihydropyridine compound is useful as an anti-inflammatory agent or the like.

13 Claims, No Drawings

PROCESS FOR PREPARING 1,4-DIHYDROPYRIDINE COMPOUNDS

The present application is a continuation of U.S. application Ser. No. 09/716,158 filed Nov. 17, 2000, now abandoned and claims priority under 35 USC 119(e) to U.S. Provisional Application 60/170,217, filed Dec. 10, 1999, the complete text of which is incorporated by reference herein, as if fully set forth.

TECHNICAL FIELD

This invention relates to a process for preparing 1,4-dihydropyridine compounds. Compounds having 1,4-dihydropyridine structure are widely used in pharmaceutical industry. The compounds have been used, for example, in treating or preventing diseases such as cardiovascular disease and inflammation diseases.

BACKGROUND ART

Nifedipine and amlodipine are well-known 1,4-dihydropyridine compounds as calcium channel blockers.

Recently, it has been discovered that certain 1,4-dihydropyridine compounds possess bradykinin antagonistic activity. For example, PCT international patent publications WO 96/06082 and WO97/30048, and U.S. Pat. No. 5,861,402 disclose 1,4-dihydropyridine compounds possessing bradykinin antagonistic activity which are thus useful in the treatment of diseases or symptoms including an inflammation disease, a cardiovascular disease, and a pain producing trauma. These bradykinin-antagonist compounds are characterized by having, at its 2-position with a substituent comprising such as carbonyl, ester, amide or imide moiety.

Various 1,4-dihydropyridine preparation processes have been disclosed. For example, Hantzsch synthesis has been widely used as a 1,4-dihydro-2,6-dimethyl-pyridine preparation process. The process can be carried out by condensation of two moles of a β-dicarbonate with one mole of an aldehyde in the presence of ammonia. J. B. Sainani reported synthesis of a 1,4-dihydro-2,6-dimethyl-pyridine compound which has asymmetrical substituents at its 3- and 5-positions (*Org. Chem. Incl. Med. Chem.* (1994), 33b (6),573–575).

BRIEF DISCLOSURE OF THE INVENTION

The present invention provides a process for preparing 1,4-dihydropyridine compounds which comprises the steps of (a) contacting an enamine compound having structure of

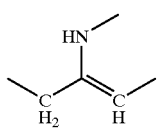

and a compound having a structure of

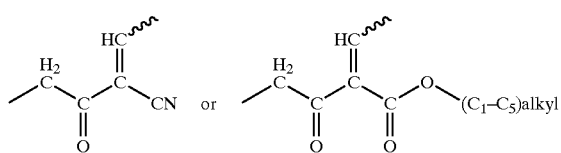

in the presence of a base; and (b) treating the reaction mixture thus obtained in the presence of an acid or a combination of acids.

The present invention also provides a process for preparing a compound of formula (I):

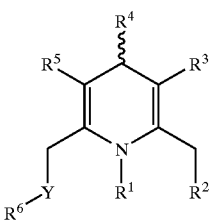

wherein
- $R^1$ is selected from hydrogen and $(C_1-C_4)$alkyl;
- $R^2$ is selected from nitrile; —$SO_3H$; —$SO_2$—$(C_1-C_6)$alkyl; —SO—$(C_1-C_6)$alkyl; —PO[O$(C_1-C_6)$alkyl]; —C(=O)—$R^7$, wherein $R^7$ is selected from hydroxy or its salt, $(C_1-C_6)$alkyl-O—, amino, $(C_1-C_6)$alkyl-NH— and di[$(C_1-C_6)$alkyl]-N—;
- $R^3$ and $R^5$ are independently selected from nitrile and $(C_1-C_5)$alkoxy-C(=O)—;
- $R^4$ is an unsubstituted or a mono-, di-, tri-, tetra- or penta-substituted phenyl wherein the substituents are independently selected from halo; $(C_1-C_4)$alkyl optionally substituted with one to three halo; $(C_1-C_4)$alkoxy optionally substituted with one to three halo; nitro; amino; mono$(C_1-C_4)$alkylamino and di[$(C_1-C_4)$alkyl]amino;
- $R^6$ is selected from hydrogen; $(C_1-C_{10})$alkyl; phenyl optionally substituted with one to two substituents independently selected from halo, $(C_1-C_4)$alkyl, trihalo$(C_1-C_4)$alkyl and $(C_1-C_4)$alkoxy; and a 4- to 10-membered heterocyclic ring containing 1 to 4 heteroatoms or heteroatom containing moieties independently selected from —O—, —S—, —NH— and —N[$(C_1-C_4)$alkyl]-, wherein said heterocyclic ring is saturated, partially-saturated or aromatic, and said heterocyclic ring is optionally substituted with one halo or $(C_1-C_4)$alkyl; and
- Y is selected from a covalent bond, methylene, oxygen and sulfur; the process comprising the steps of
  - (a) addition reaction of an enamine compound of formula

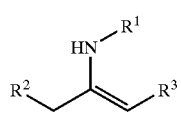

to a compound of formula

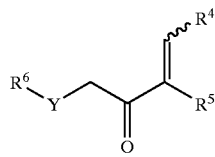

wherein $R^1$, $R^2$, $R^3$, $R^4$, $R^5$, $R^6$ and Y are as defined above in the presence of a base under reaction conditions sufficient for coupling the compounds; and
  - (b) cyclization of the resulting compound in step (a) in the presence of an acid catalyst selected from a protonic acid, and a combination of a protonic acid and a non-protonic Lewis acid.

In the above described processes, compounds of formula (I) or (II) wherein $R^2$ is a salt of carboxyl group (i.e., $R^2$ is —C(=O)—$R^7$ wherein $R^7$ is a salt of hydroxy) are inorganic or organic salts of the carboxylic acid. Those salts are formed with a cation such as alkali or akaline earth metal (e.g., sodium, potassium, calcium, and magnesium), hydroxide or alkoxide in water or an appropriate organic solvent such as ethanol, isopropyl alcohol or mixture thereof.

According to the present invention, in general, desired 1,4-dihydropyridine compounds can be prepared under mild conditions, in a one-pot synthesis and high-yield.

In the above process, preferred substrates of formula (II) and resulting compounds of formula (I) are those compounds of each formula wherein $R^1$ is hydrogen.

DETAILED DISCLOSURE OF THE INVENTION

The term "$(C_1-C_4)$alkyl", as used herein, unless otherwise indicated, means a straight or branched saturated monovalent hydrocarbon radical selected from methyl, ethyl, propyl, isopropyl, n-butyl, sec-butyl and tert-butyl.

The term "$(C_1-C_4)$alkoxy", as used herein, unless otherwise indicated, means a straight or branched $(C_1-C_4)$alkyl-O radical selected from methoxy, ethoxy, propoxy, isopropoxy, n-butoxy, sec-butoxy and tert-butoxy.

The term "heterocyclic ring", as used herein, unless otherwise indicated, means a monocyclic or bicyclic hydrocarbon group which has one or more hetero atoms in the ring, preferably has 6 to 9 carbon atoms and 1 to 4 hetero atoms or independently selected from —O—, —S—, —NH—, —N[$(C_1-C_4)$alkyl]-, wherein said heterocyclic is saturated, partially-saturated or aromatic. Examples of those groups include, but not limited to piperidino, morpholino, thiamorphorino, pyrrolidino, pyrazolino, pyrazolidino, pyrazoryl, piperazinyl, furyl, thienyl, oxazolyl, tetrazolyl, thiazolyl, imidazolyl, pyrazolyl, pyridyl, pyrimidinyl, pyrrolyl, pyrrolidinyl, quinolyl and quinuclidinyl.

The term "halo", as used herein, refers to F, Cl, Br or I, preferably F or Cl.

Preferred bases used in reaction step (a) of this invention include bases capable of promoting a Michael-type reaction.

Preferred combination of "base in step (a)" and "acid catalyst in step (b)" may be "a magnesium (II) base in step (a)" and "a protonic acid in step (b)".

Preferably, an amount of the base is equal or more than 1 equivalent.

Other preferred combination of "base in step (a)" and "acid catalyst in step (b)" may be "bases other than magnesium (II) bases (e.g., alkyl-magnesium-halides, halomagnesium-alkoxides and magnesium-dialkoxides) which are capable of promoting a Michael-type reaction in step (a)" and "a combination of a protonic acid and a non-protonic Lewis acid". Any non-protonic Lewis acids known to those skilled in the art such as metal halides, metal triflates (i.e., metal trifluoromethanesulfonate) or the like may be used in step (b). Examples of the Lewis acid include magnesium bromide, magnesium chloride, zinc bromide, zinc chloride, zinc iodide, tin(IV) chloride, titanium(IV) chloride, aluminium trichloride, ethylaluminum dichloride, diethylaluminum chloride, boron trifluoride, copper(II) triflate, scandium(III) triflate, lanthanum triflate, ytterbium triflate, lanthanum chloride, cerium(III) chloride and iron (III) chloride. Preferred individual Lewis acids include magnesium bromide and its ether complex such as magnesium bromide diethyl etherate, magnesium chloride and its ether complex such as magnesium chloride diethyl etharate, zinc chloride, zinc bromide and scandium(III) triflate. Among the Lewis acids, preferred ones include magnesium (II) salts such as magnesium halides, magnesium bromides and their ether complexes such as magnesium bromide diethyl etherate. Another preferred ones include magnesium (II) salts such as a magnesium sulfate, magnesium acetate, halomagnesiumacetate and halomagnesium sulfate.

Non-protonic Lewis acid such as $MgCl_2$ can be added in the step (a) in advance.

When the starting compounds contain Lewis basic atom (s) such as N and O, an amount of the Lewis acid added may be increased for the success of step (b).

Preferably, a process of this invention may be carried out under reaction conditions wherein reaction step (a) is carried out in a reaction inert solvent at a temperature in the range from −150° C. to the reflux temperature of the reaction mixture for 3 minutes to 2 days; and reaction step (b) is carried out in a reaction inert solvent at a temperature in the range from −150° C. to the reflux temperature of the reaction mixture for 1 second to 5 days.

More preferably, a process of this invention may be carried out under reaction conditions wherein the reaction step (a) is carried out in a reaction inert solvent at a temperature in the range from −40° to 80° C. for 1 minute to 40 hours; and the reaction step (b) is carried out in a reaction inert solvent at a temperature in the range from −40° to 80° C. for 1 minute to 5 days.

Preferred bases used in reaction step (a) of this invention include $(C_1-C_4)$alkyllithiums, halomagnesium$(C_1-C_4)$ alkoxide, $(C_1-C_6)$alkylmagnesiumhalides, metalhydrides, metal$(C_1-C_3)$alkoxides, metal-n-butoxide, metal-sec-butoxide, metal-tert-butoxide, metalcarbonate and metalfluoride.

Preferred acids used in reaction step (b) of this invention include hydrochloric acid, toluene (p-, m- or o-toluene) sulfonic acid, phosphoric acid, sulfuric acid, nitric acid and $(C_1-C_6)$alkanoic acid.

Preferred process of this invention include a compound of formula (I):

wherein $R^1$ is selected from hydrogen, methyl and ethyl;

$R^2$ is selected from —C(=O)—$R^7$, wherein $R^7$ is selected from hydroxy or its salt, $(C_1-C_6)$alkyl-O—, amino, $(C_1-C_6)$alkyl-NH— and di[$(C_1-C_6)$alkyl]-N—;

$R^3$ and $R^5$ are independently $(C_1-C_3)$alkoxy-C(=O)—;

$R^4$ is di-substituted phenyl wherein the substituents are independently selected from halo, $(C_1-C_4)$alkyl optionally substituted with one to two halo, and nitro;

$R^6$ is selected from hydrogen; $(C_1-C_5-)$alkyl; phenyl optionally substituted with one to two substituents independently selected from halo, $(C_1-C_4)$alkyl, $CF_3$ and $(C_1-C_4)$alkoxy; and a 4- to 10-membered heterocyclic ring selected from piperidino, morpholino, thiamorphorino, pyrrolidino, pyrazolino, pyrazolidino, pyrazoryl, piperazinyl, furyl, thienyl, oxazolyl, tetrazolyl, thiazolyl, imidazolyl, pyrazolyl, pyridyl, pyrimidinyl, pyrrolyl, pyrrolidinyl, quinolyl and quinuclidinyl, and said heterocyclic ring being optionally substituted with one halo or $(C_1-C_4)$alkyl; and Y is selected from a covalent bond, methylene, oxygen and sulfur.

Preferred process of this invention include a compound of formula (I):
wherein
$R^1$ is hydrogen; $R^2$ is COOH, $COOCH_3$ or $COOC_2H_5$;
$R^3$ and $R^5$ are independently COOH, $COOCH_3$ or $COOC_2H_5$;
$R^4$ is a mono- or di-substituted phenyl wherein substituents are independently selected from fluoro, chloro and nitro;
$R^6$ is selected from hydrogen; $(C_1-C_3)$alkyl; phenyl optionally substituted with one to two substituents independently selected from halo, $(C_1-C_3)$alkyl, $CF_3$ and $(C_1-C_3)$alkoxy; and a 4- to 10-membered heterocyclic ring selected from piperidino, morpholino, thiamorphorino, pyrrolidino, pyrazolino, pyrazolidino, pyrazoryl, piperazinyl, furyl, thienyl, oxazolyl, tetrazolyl, thiazolyl, imidazolyl, pyrazolyl, pyridyl, pyrimidinyl, pyrrolyl, pyrrolidinyl, quinolyl and quinuclidinyl, and said heterocyclic ring being optionally substituted with one halo or $(C_1-C_3)$alkyl; and
Y is a covalent bond or methylene.

The following reaction schemes and discussion illustrate the preparation process of the present invention for preparing a compound of formula (I). Unless otherwise indicated, $R^1$ through $R^8$, Y, and p, q and r in the reaction schemes and discussion that follow are defined above. In the each reaction described below, unless otherwise indicated, the reaction pressure is not critical. Generally, the reactions will be conducted at a pressure of about one to about three atmospheres, preferably at ambient pressure (about one atmosphere). Also, unless otherwise indicated, the reactions run at about room temperature (i.e., from about 20° to 25° C.).

Compounds of formula (I) may be prepared by a process of this invention according to Scheme 1.

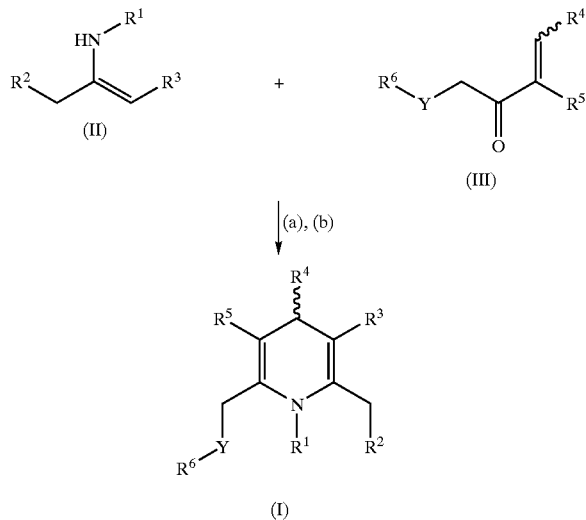

Scheme 1 exemplifies a process of this invention for preparing a compound of formula (I) comprising step (a): addition of an enamine compound of formula (II) to an alkylene compound of formula (III) followed by step (b) acid catalyzed cyclization reaction of the resulting compound in step (a).

The former addition step (a) may be carried out under conditions applied to nucleophilic addition reactions using a suitable base in a reaction inert solvent. More preferably, the reaction may be carried out under conditions commonly used in Michael-type addition. Preferred bases for this reaction are those used in Michael-type reactions. Examples of the preferred bases include alkylmagnesium halides known as Grignard reagents and halomagnesium alkoxides. More preferred bases include $(C_1-C_6)$alkylmagnesium bromide and tert-butoxy-magnesium bromide. Preferred solvents used in this reaction include $(C_1-C_4)$alkanol, tetrahydrofuran (THF), diethyl ether, dioxane, hexane, toluene, 1,2-dimethoxy ethane (DME) and the like. This reaction may be carried out at a temperature from about $-150°$ C. to reflux, preferably from about $-100°$ to $100°$ C. In view of convenience, this reaction may be carried out at about room temperature using, for example, halomagnesium$(C_1-C_4)$ alkoxides, $(C_1-C_6)$alkylmagnesiumhalides, metalhydrides, metal$(C_1-C_3)$alkoxides, magnesium-di[$(C_1-C_3)$alkoxides], metal-n-butoxide, metal-sec-butoxide, metal-tert-butoxide, a metalcarbonate such as $K_2CO_3$, or metalamide such as $R_2N$—M wherein R is $C_{1-4}$ alkyl or —Si$(C_{1-3}$ alkyl$)_3$; and M is Li, Na, Mg or K (Preferably, halomagnesium$(C_1-C_4)$ alkoxide or $(C_1-C_6)$alkylmagnesiumhalides). In case of the base is $K_2CO_3$, the reaction is effectively run in THF. In case of the base is CsF or KF, the reaction is effectively run in THF or methanol (MeOH) at an elevated temperature such as at about 60° C. In case of using butyllithium (BuLi), the reaction is effectively run in THF at from about $-78°$ C. to about $-30°$ C. In case of using halomagnesium$(C_1-C_4)$ alkoxides or $(C_1-C_6)$alkylmagnesiumhalides, a preferred solvent is THF. Suitable reaction time ranges from about 3 minutes to about 2 days, preferably from about 30 minutes to about 40 hours.

The subsequent cyclization process step (b) may be carried out in the presence of a protonic acid. Suitable protonic acids include $(C_1-C_6)$alkanoic acid such as acetic acid, hydrochloric acid (HCl) and sulfonic acids such as p-toluenesulfonic acid. It is preferred to add a non-protonic Lewis acid to the reaction mixture in combination with the protonic acid, when the base used in Step (a) is other than magnesium (II) bases. This reaction may be carried out at a temperature from about $-150°$ C. to reflux, preferably from about $-100°$ to $100°$ C. The reaction time ranges from about 1 second to 5 days, preferably 5 minutes to 20 houres.

Generally, those reactions illustrated in Scheme 1 may be carried out at about $-78°$ C. using dry-ice/acetone or dry-ice/methanol, about 0° C. using an ice-bath, room temperature or 100° C. preferably at about 0° C. or about room temperature.

The reaction steps (a) and (b) are performed in the same reaction vessel under mild conditions with high-yield.

An enamine compound of formula (II) may be prepared according to procedures known to those skilled in the art, such as those illustrated in Scheme 2.

Scheme 2

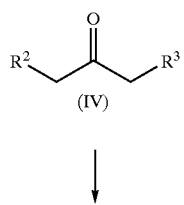

-continued

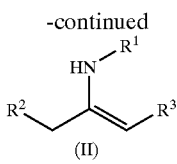

(II)

Typically, a beta-keto ester compound of formula (IV) may be transformed to a compound of formula (II) wherein $R^2$ and $R^3$ are defined as above. This reduction may be carried out in a reaction inert solvent resolving ammonia gas at a temperature in the range of from about 0° to 60° C. Suitable reaction inert solvents include lower, alkanols such as methanol and ethanol. Alternatively, an ammonia gas containing solution given above may be added to a solution containing a beta-keto ester (IV). The mixture is reacted at a temperature in the range of from about 0° to 60° C. to yield the enamine compound (II).

An alkylene compound of formula (III) may be prepared according to procedures known to those skilled in the art. Scheme 3 illustrates one embodiment of the preparation process.

Scheme 3

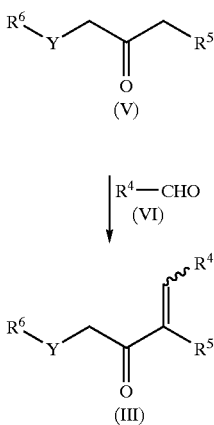

A carbonyl compound of formula (V) may be subjected to a coupling reaction with an aldehyde compound of formula (VI) to give the alkylene compound of formula (III) according to a known procedure. For example, a compound of formula (V) wherein $R^6$—Y— is an optionally substituted heterocyclic-$(CH_2)_2$— may be reacted with a compound of formula (VI) according to a procedure reported by L. Tietze et al. Liebigs Ann. Chem., pp. 321–329, 1988. This reaction may be carried out in a suitable reaction inert-solvent for example an aromatic hydrocarbon such as benzene, toluene and xylene, an alcohol such as methanol, ethanol, propanol and butanol, an ether such as diethyl ether, dioxane and tetrahydrofuran (THF), a halogenated hydrocarbon such as methylene dichloride, chloroform and dichloroethane, an amide such as N,N-dimethylformamide, and a nitrile such as acetonitrile. This reaction may be carried out at a temperature in the range of from about 0° C. to the reflux temperature of the reaction mixture, preferably from about 80° to the 120° C. for from about 30 minutes to 24 hours, preferably from 30 minutes to 6 hours. This reaction may conveniently be carried in the presence of a base or acid catalyst. Suitable base catalysts are such as piperidine, pyridine and alkoxide, and suitable acid catalysts are such as acetic acid, $TiCl_4$ and p-toluenesulfonic acid.

An intermediate compound of formula (V) may be prepared starting from a known compound according to a procedure known to those skilled in the art. For example, a compound of formula (V) wherein $R^6$ is an optionally substituted heterocyclic (including heteroaryl) defined as above, and $R^3$ is $(C_1-C_1)$alkoxy-C(=O)— may be prepared according to the procedure described in Scheme 4.

Scheme 4

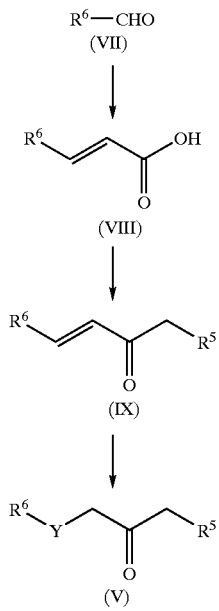

An aldehyde compound (VII), wherein $R^6$ is defined as above, is reacted with malonic acid under a basic condition. For example, this reaction may be carried out in the presence of a weak base such as piperidine in a reaction inert solvent such as pyridine to give a carboxylic acid compound of formula (VIII). The compound (VIII) thus obtained may be subjected to an aliphatic nucleophilic substitution reaction in the presence of a coupling agent to give a pentenoate compound of formula (IX). This reaction may conveniently be carried out first by treating the compound of formula (VII) with a coupling agent such as N,N'-carbonyldiimidazole in a reaction inert solvent such as dimethylformamide, then reacting with a neucleophilic reagent such as $CH_3O_2CCH_2K$ in the presence of a Lewis acid such as magnesium chloride. The former treatment may be carried out at a temperature in the range of from about 0° to 60° C. preferably at about room temperature for from about 1 minutes to 12 hours. The latter reaction may be carried out at the temperature in the range of from about 0° to 100° C., preferably from about room temperature to 60° C. for from about 1 minutes to 12 hours. The compound of formula (IX) may be reduced over a metal catalyst under hydrogen atmosphere to give the compound of formula (V) according to a known procedure. Suitable catalysts are such as Raney nickel catalyst and a noble metal catalysts including palladium on carbon and palladium hydroxide. This reaction may be carried out in a reaction inert solvent such as methanol, at about room temperature under hydrogen at an appropriate pressure for example using a balloon, for about 1 minutes to 12 hours.

A ketone compound of formula (V) and a substituted benzaldehyde compound of formula (VI) may also be prepared according to known procedures (e.g., (1) D. Scherling, J. Labelled Compds. Radiopharm., Vol. 27, pp. 599-, 1989, (2) C. R. Holmquist et al., J. Org. Chem., Vol. 54, pp. 3528-, 1989, (3) S. N. Huckin et al., J. Am. Chem. Soc., Vol. 96, pp.

1082-, 1974, (4) *J. C. S. Perkin I*, pp. 529-, 1979, (5) *Synthesis* pp. 37, 1986, and (6) *J. C. S. Chem. Commun.*, pp. 932-, 1977).

Compounds of formula (I) have a chiral center, and, if required, an enantiomeric mixture of the compounds may be separated by procedures known to those skilled in the art (e.g., using H.P.L.C. or fractional crystallization). Also, an enantiomeric mixture of compounds of formula (III) may be optically separated by the similar methods prior to being subjected to the preparation processes of this invention.

Compounds of formula (I) prepared according to the procedures described as above may be isolated and purified by conventional procedures such as recrystallization or chlomatographic purification.

Compounds of formula (I) thus obtained may further be subjected to desired reactions. For example, the compounds wherein $R^2$ is —COOH, may be subjected to coupling reactions with a desired amine or imine compounds to give such compounds as disclosed in WO 96/06082, WO 97/30048, U.S. Pat. No. 5,861,402 or the like.

With the processes of the present invention, 1,4-dihydropyridine compounds can be effectively prepared under mild conditions. Especially, 1,4-dihydropyridine compunds which are difficult to be synthesized by Hantzsch method (not under mild conditions), can be synthesized because of the mild conditions in the present invention.

EXAMPLE

The invention is illustrated in the following non-limiting example in which, unless stated otherwise: all operations were carried out at room or ambient temperature, that is, in the range of 18–25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given were uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254s}$ precoated HPTLC plates), mass spectrometry, nuclear magnetic resonance (NMR), infrared red absorption spectra (IR) or microanalysis. Yields were given for illustrative purposes only. Flash column chromatography was carried out using Merck silica gel 60 (230–400 mesh ASTM) or Fuji Silysia Chromatorex® DU3050 (Amino Type, 30–50 μm). Low-resolution mass spectral data (EI) were obtained on an Automass 120 (JEOL) mass spectrometer. Low-resolution mass spectral data (ESI) were obtained on a Quattro II (Micromass) mass spectrometer. NMR data was determined at 270 MHz (JEOL JNM-LA 270 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.). Chemical symbols have their usual meanings; b.p. (boiling point), m.p. (melting point), l (liter(s)), ml (milliliter(s)), g (gram(s)), mg(milligram(s)), mol (moles), mmol (millimoles), eq. (equivalent(s)).

A. Methyl 3-oxo-5-(1,3-thiazole-2-yl)-4-pentenoate

Methyl 3-oxo-5-(1,3-thiazole-2-yl)-4-pentenoate was prepared from 3-(1,3-thazol-2-yl)-2-propenic acid (*Bull. Chem. Soc. Jap.* 1974, 47, 151.) according to the literature procedure (*Heterocycles* 1994, 38, 751.). To a stirred solution of 3-(1,3-thiazol-2-yl)-2-propenoic acid (100.0 g, 644.4 mmol) in DMF (1000 ml) was added 1,1'-carbonyldiimidazole (115.0 g, 708.9 mmol) in small portions. After stirring at room temperature for 5 h, to the reaction mixture were added anhydrous magnesium chloride (73.6 g, 773.0 mmol) and monomethyl malonate potassium salt (120.8 g, 773.0 mmol). The resulting suspension was heated at 55° C. with stirring for 14 h. After cooling to room temperature, the reaction mixture was poured into 1500 ml of 2 N HCl, and extracted with a mixture of EtOAc (1500 ml) and toluene (500 ml). The organic phase was separated and the aqueous phase was extracted with a 3:1 mixture of EtOAc and toluene (2000 ml). The combined organic phase was washed with $H_2O$ (1000 ml) and brine (1000 ml), dried ($Na_2SO_4$) and evaporated to afford 132.0 g of methyl 3-oxo-5-(1,3-thiazole-2-yl)-4-pentenoate (½ of keto/enol form)

$^1$H NMR (CDCl$_3$) δ: 11.77 (s, ⅔ H), 7.97 (d, J=3.1 Hz, ⅓ H), 7.90 (d, J=3.1 Hz, ⅔ H), 7.72 (d, J=16.0 Hz, ⅓ H), 7.55 (d, J=15.6 Hz, ⅔ H), 7.51 (d, J=3.1 Hz, ⅓ H), 7.39 (d, J=3.1 Hz, ⅔ H), 7.06 (d, J=16.0 Hz, ⅓ H), 6.80 (d, J=15.6 Hz, ⅔ H), 5.28 (s, ⅔ H), 3.79 (s, 3×⅔ H), 3.77 (s, 3×⅓ H), 3.45 (s, 2×⅓ H).

B. Methyl 3-oxo-5-(1,3-thiazole-2-yl)pentanoate

A mixture of methyl 3-oxo-5-(1,3-thiazole-2-yl)-4-pentenoate (132.0 g) and palladium hydroxide, 20 wt % on carbon (13 g) in MeOH (2600 ml) was stirred under hydrogen atmosphere by balloon at room temperature for 4 h. Catalyst was removed by filtration and the filtrate evaporated to give 130.0 g of methyl 3-oxo-5-(1,3-thiazole-2-yl) pentanoate as a brown liquid.

$^1$H NMR (CDCl$_3$) δ:7.65 (d, J=3.3 Hz, 1 H), 7.20 (d, J=3.3 Hz, 1 H), 3.73 (s, 3 H), 3.53 (s, 2 H), 3.33 (t, J=6.9 Hz, 2 H), 3.13 (t, J=6.9 Hz, 2 H).

C. Methyl 3-(2,6-dichlorophenyl)-2-[(1,3-thiazol-2-yl)propanoyl]-2-propenoate

To a solution of methyl 3-oxo-5-(1,3-thiazole-2-yl) pentanoate (130 g) in toluene (600 ml) were added 2,6-dichlorobenzaldehyde (113.0 g, 644 mmol), acetic acid (5 ml) and piperidine (5 ml). This mixture was distilled for removal of the initial distillate (about 100 ml) then replaced the distillation apparatus to Dean-Stark trap and heated under reflux temperature with azeotropic removal of $H_2O$ for 4 h. The mixture was washed with $H_2O$ (200 ml) and brine (200 ml), dried (Na2SO$_4$) and evaporated to give a crude mixture. This was purified by column chromatography on silica gel (1800 g, hexane/EtOAc=3/1 as eluent) to afford 165.3 g (69%, 3 steps) of methyl 3-(2,6-dichlorophenyl)-2-[1,3-thiazol-2yl)propanoyl]-2-propenote as a brown oil. This is a 1:1 mixture of the double bond isomers.

$^1$H NMR (CDCl$_3$) δ:7.70–7.15 (m, 6 H), 3.91 and 3.66 (apparently two synglets, 3 H), 3.44 and 3.28 (apparently two synglets, 4 H).

D. Dimethyl 4-(2,6-dichlorophenyl)-2-(2-methoxy-2-oxoethyl)-6-[2-(1,3-thiazol-2-yl)ethyl]-1,4-dihydropyridine-3,5-dicarboxylate To a stirred solution of 2-methyl-2-propanol (92.8g, 1252 mmol; 2.1 eq.) in anhydrous THF (1100 ml) was added a 1.0M solution of EtMgBr in THF (1192 ml, 1192 mmol; 2.0 eq.) dropwise slowly at 0° C. under nitrogen atmosphere for 2 h period. The resulting solution was stirred at room temperature for 1 h. Then to the mixture was added a solution of dimethyl 3-amino-2-pentenedioate (113.5 g, 655 mmol; 1.1 eq.) in anhydrous THF (550 ml) dropwise slowly at 0° C. for 20 min. The resulting pale yellow solution was stirred at the same temperature for 1 h, then a solution of methyl 3-(2,6-dichlorophenyl)-2-[(1,3-thiazol-2-yl) propanoyl]-2-propenoate (219.9 g, 594 mmol; 1.0 eq.) in anhydrous THF (550 ml) was added at 0° C. for 30 min. The reaction mixture was stirred at room temperature for 16 h under nitrogen atmosphere, then acetic acid (170 ml; 5.0 eq.) was added at 0° C. The resulting mixture was stirred at room temperature for 6 h. The mixture was poured into 2N NaOHaq. (1000 ml), the organic phase was separated and the aqueous phase was extracted with EtOAc (2000 ml). The combined organic phase was washed with $H_2O$ (1000 ml) and brine (1000 ml), dried ($Na_2SO_4$) and concentrated to give a crude mixture. Purification on silica gel column chromatography (3 times 1700 g) eluted with hexane/EtOAc (2/1 to 1/2) to afford 246.0 g (85%) of dimethyl 4-(2,6-dichlorophenyl)-2-(2-methoxy-2-oxoethyl)-6-[2-(1,3-thiazol-2-yl)ethyl]-1,4-dihydropyridine-3,5-dicarboxylate as a brown oil $^1$H NMR (CDCl$_3$) δ:8.33 (s, 1 H), 7.67 (d, J=3.3 Hz, 1 H), 7.24 (t, J=8.0 Hz, 2 H), 7.24 (d, J=3.3 Hz, 1 H), 6.98 (dd, J=8.0, 8.0 Hz, 1 H), 5.99 (s, 1 H), 3.86–3.65 (m, 5 H), 3.51 (s, 3 H), 3.54 (s, 3 H), 3.45–3.25 (m, 3 H), 3.14–2.96 (m, 1 H).

In Step D in the above working example, the coupling in the presence of the magnesium base and the subsequent cyclization in the presence of acidic acid occurred as a one-pot synthesis.

What is claimed is:

1. A process for preparing 1,4-dihydropyridine compounds which comprises the steps of (a) contacting an enamine compound having a structure of

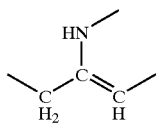

and a compound having a structure of

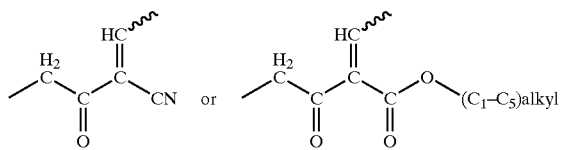

in the presence of a base; and (b) treating the reaction mixture thus obtained in the presence of an acid or a combination of acids.

2. A process according to claim 1 for preparing a compound of Formula (I):

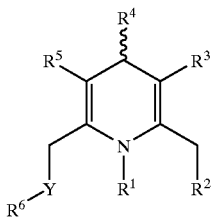

wherein
$R^1$ is hydrogen or $(C_1-C_4)$alkyl;
$R^2$ is nitrile; $-SO_3H$; $-SO_2-(C_1-C_6)$alkyl; $-SO-(C_1-C_6)$alkyl; $-PO[O(C_1-C_4)$alkyl$]_2$; $-C(=O)-R_7$, wherein $R^7$ is hydroxy or its salt, $(C_1-C_6)$alkyl-O—, amino, $(C_1-C_6)$alkyl-NH— or di$[(C_1-C_6)$alkyl-N—;

$R^3$ and $R^5$ are independently nitrile or $(C_1-C_5)$alkoxy-C(=O)—;
$R^4$ is an unsubstituted or a mono-, di-, or tri-, tetra- or penta-substituted phenyl wherein the substituents are independently halo; $(C_1-C_4)$alkyl optionally substituted with one to three halo; $(C_1-C_4)$alkoxy optionally substituted with one to three halo; nitro; amino; mono$(C_1-C_4)$alkylamino or di$[(C_1-C_4)$alkyl]amino;
$R^6$ is selected from the group consisting of hydrogen; $(C_1-C_{10})$alkyl; phenyl optionally substituted with one to two substituents independently selected from the group consisting of halo, $(C_1-C_4)$alkyl, trihalo $(C_1-C_4)$alkyl and $(C_1-C_4)$alkoxy; and a 4- to 10-membered heterocyclic ring containing 1 to 4 heteroatoms or heteroatom containing moieties independently selected from the group consisting of —O—, —S—, —NH— and —N$[(C_1-C_4)$alkyl]-, wherein said heterocyclic ring is saturated, partially-saturated or aromatic, and said heterocyclic ring is optionally substituted with one halo or $(C_1-C_4)$alkyl; and
Y is a covalent bond, methylene, oxygen or sulfur; the process comprising the steps of
(a) addition reaction of an enamine compound of formula II

to a compound of formula III

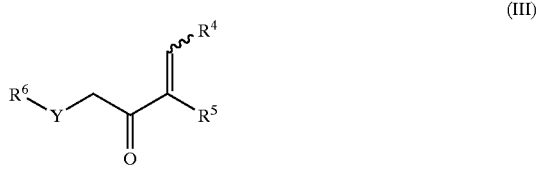

wherein $R^1$, $R^2$, $R^3$, $R^4$, $R^5$, $R^6$ and Y are as defined above1 in the presence of a base under reaction conditions sufficient for the addition reaction of the compounds; and
(b) cyclization of the resulting compound of step (a) in the presence of an acid catalyst selected from the group consisting of a protonic acid, and a combination of a protonic acid and a non-protonic Lewis acid.

3. A process of claim 1 wherein the base in reaction step (a) is a base capable of promoting a Michael-type reaction.

4. A process of claim 1 wherein the base in reaction step (a) is a magnesium (II) base and the acid catalyst in reaction step (b) is a protonic acid.

5. A process of claim 1 wherein the base in reaction step (a) is other than magnesium (II) bases and the acid catalyst in step (b) is a combination of a protonic acid and a non-protonic acid Lewis acid.

6. A process of claim 1 wherein the reaction step (a) is carried out in a reaction inert solvent at a temperature in the range from −150° C. to the reflux temperature of the reaction mixture for 3 minutes to 2 days, and the reaction step (b) is carried out in a reaction inert solvent in a temperature in the range from −150° C. to the reflux temperature of the reaction mixture for 1 second to 5 days.

7. A process of claim 6 wherein the reaction step (a) is carried out in the reaction inert solvent at a temperature in the range from −40° to 80° C. for 1 minute to 40 hours, and the reaction step (b) is carried out in a the reaction inert solvent at a temperature in the range from −40° to 80° C. for 1 minute to 5 days.

8. A process of claim 1 wherein the base in reaction step (a) is $(C_1-C_4)$alkyllithiums, halomagnesium$(C_1-C_4)$ alkoxides, $(C_1-C_6)$alkylmagnesiumhalides, metalhydrides, metal$(C_1-C_3)$alkoxides, magnesium-di[$(C_1-C_3)$alkoxides], metal-n-butoxides, metal-sec-butoxides, metal-tert-butoxides, metalcarbonates and metalfluorides.

9. A process of claim 1 wherein the acid catalyst in reaction step (b) is hydrochloric acid, p-toluene sulfonic acid, phosphoric acid, sulfuric acid, nitric acid or $(C_1-C_6)$ alkanoic acid.

10. A process according to claim 2 wherein $R^1$ is hydrogen, methyl or ethyl;

$R^2$ is —C(=O)—$R^7$, wherein $R^7$ is hydroxy or its salt, $(C_1-C_6)$alkyl-O—, amino, $(C_1-C_6)$alkyl-NH— or di[$(C_1-C_6)$alkyl]-N—;

$R^3$ and $R^5$ are independently $(C_1-C_3)$alkoxy-C(=O)—;

$R^4$ is di-substituted phenyl wherein the substituents are independently halo, $(C_1-C_4)$alkyl optionally substituted with one or two halo, or nitro;

$R^6$ is hydrogen; $(C_1-C_5)$alkyl; phenyl optionally substituted with one to two substituents independently selected from the group consisting of halo, $(C_1-C_4)$ alkyl, $CF_3$ and $(C_1-C_4)$alkoxy; and a 4- to 10-membered heterocyclic ring selected from the group consisting of piperidino, morpholino, thiamorphorino, pyrrolidino, pyrazolino, pyrazolidino, pyrazoryl, piperazinyl, thiryl, thienyl, oxazolyl, tetrazolyl, thiazolyl, imidazolyl, pyrazolyl, pyridyl, pyrimidinyl, pyrrolyl, pyrrolidinyl, quinoyl and quinuclidinyl, and said heterocyclic ring being optionally substituted with one halo or $(C_1-C_4)$alkyl; and Y is a covalent bond, methylene, oxygen or sulfur.

11. A process according to claim 10 wherein $R^1$ is hydrogen; $R^2$ is COOH, $COOCH_3$ or $COOC_2H_5$;

$R^3$ and $R^5$ are independently COOH, $COOCH_3$ or $COOC_2H_5$;

$R^4$ is a mono- or di-substituted phenyl wherein substituents are independently selected from fluoro, chloro and nitro;

$R^6$ is selected from hydrogen; $(C_1-C_3)$alkyl; phenyl optionally substituted with one to two substituents independently selected from halo, $(C_1-C_3)$alkyl, $CF_3$ and $(C_1-C_3)$alkoxy; and a 4- to 10-membered heterocyclic ring selected from piperidino, morpholino, thiamorphorino, pyrrolidino, pyrazolino, pyrazolidino, pyrazoryl, piperazinyl, furyl, thienyl, oxazolyl, tetrazolyl, thiazolyl, imidazolyl, pyrazolyl, pyridyl, pyrimidinyl, pyrrolyl, pyrrolidinyl, quinolyl and quinuclidinyl, and said heterocyclic ring being optionally substituted with one halo or $(C_1-C_3)$alkyl; and Y is a covalent bond or methylene.

12. A process according to claim 5 wherein the non-protonic Lewis acid is a metal halide or a metal trifluoromethanesulfonate.

13. A process according to claim 5 wherein the non-protonic Lewis acid is a magnesium (II) salt.

* * * * *